US00PP17126P2

(12) United States Plant Patent
Warner

(10) Patent No.: US PP17,126 P2
(45) Date of Patent: Oct. 3, 2006

(54) CLIMBER ROSE PLANT NAMED 'CHEWGOLDTOP'

(50) Latin Name: *Rosa hybrida*
Varietal Denomination: CHEwgoldtop

(75) Inventor: Christopher H. Warner, Newport (GB)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/171,600

(22) Filed: Jun. 29, 2005

(51) Int. Cl.
*A01H 5/00* (2006.01)

(52) U.S. Cl. ..... Plt./111

(58) Field of Classification Search ..... Plt./111
See application file for complete search history.

*Primary Examiner*—Kent Bell
*Assistant Examiner*—June Hwu
(74) *Attorney, Agent, or Firm*—Klarquist Sparkman LLP

(57) ABSTRACT

Climber rose plant having large, yellow flowers produced on long climbing canes; moderate spicy scent; recurrent bloom; and resistance to rust and powdery mildew.

1 Drawing Sheet

Genus and species: *Rosa hybrida.*
Variety denomination: 'CHEwgoldtop'.

ORIGIN OF THE INVENTION

The present invention relates to a new and distinct variety of a climber rose plant named 'CHEwgoldtop' which was originated by me by crossing the variety 'CHEwarvel' (Laura Ford aka King Tut), U.S. Plant Pat. No. 9,012, with the variety 'BEEsian' (Amanda), (unpatented).

BACKGROUND OF THE INVENTION

The primary objective of this breeding was to produce a new rose variety having large yellow flowers, climbing canes and some fragrance. Also desired was good disease resistance.

BRIEF SUMMARY OF THE INVENTION

These objectives were substantially achieved, along with other desirable improvements, as evidenced by the following unique combination of characteristics that are outstanding in the new variety and that distinguish it from its parents, as well as from all other varieties of which I am aware:

1. Large, yellow flowers produced on long climbing canes.
2. Moderate spicy scent.
3. Recurrent bloom.
4. Resistance to rust and powdery mildew.

Asexual reproduction of this new variety by cuttings, as performed at Wasco, Calif. and at Newport, Shropshire, England, shows that the foregoing and all other characteristics and distinctions come true to form and are established and transmitted through succeeding propagations.

COMPARISON WITH PARENTS

The female parent has smaller flowers, smaller leaves and less fragrance than 'CHEWgoldtop'. The male parent does not climb.

COMPARISON WITH SIMILAR VARIETY

The subject variety most closely resembles Golden Showers (U.S. Plant Pat. No. 1,557). It differs from Golden Showers in having much lighter, well-formed flowers, more scent (spicy versus sweet for Golden Showers) and has more dense foliage and superior disease resistance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'CHEWarvel' (Laura Ford aka King Tut), U.S. Plant Pat. No. 9,012.
*Pollen parent.*—'BEEsian' (Amanda), (Not patented).

FLOWER

Observations were made of plants commencing at four years of age grown on their own roots in a garden environment at Somis, Calif. from January 2003 to September 2004.

Blooming habit: Continuous.
Bud:
*Size.*—About 35–40 mm long and 20–25 mm in diameter when the petals start to unfurl.
*Form.*—The bud form is long, pointed ovoid.
*Color.*—When sepals first divide, bud color is Yellow-Orange Group 15C. When half blown, the upper sides of the petals are close to Yellow Group 12B;

and the lower sides of the petals are Yellow Group 12C.

*Sepals.*—Color: Upper surface: Green Group 138B. Lower surface: Green Group 137D. Length: 25 mm. Width: 10 mm. Shape: Acuminate. Surface texture: Hoary. There are three normally appendaged sepals. There are two unappendaged sepals with hairy edges.

*Receptacle.*—Color: Green Group 137C. Shape: Funnel. Size: Medium, about 7 mm long×5 mm wide. Surface: Smooth.

*Peduncle.*—Length: Short, averaging about 40 mm long. Surface: Smooth. Color: Yellow-Green Group 146C. Strength: Stiff, erect.

Bloom:

*Size.*—Large. Average open diameter is about 10 cm.

*Borne.*—Sereral together in pyramidal clusters of 3–5 blooms.

*Stems.*—Strength: Strong. Average length is about 150 cm for main climbing canes and 25–30 cm for flowering side shoots with a diameter of 6–7 mm.

*Form.*—When first open: High centered. Permanence: Outer petals curl back.

*Petalage.*—Number of petals under normal conditions: 25.

*Color.*—The upper sides of the petals are Yellow Group 12B. The reverse sides of the petals are Yellow Group 12C. The base of each petal has a 3 mm×3 mm Yellow Group 13A color spot. The major color on the upper side is Yellow Group 12B.

*Variegations.*—None observed.

*Discoloration.*—The general tonality at the end of the first day: No change. At the end of the third day: No change. Further aging: By day five, there is fading on the outer petal edges to Yellow Group 12C and by day six or seven to Yellow Group 12D.

*Fragrance.*—Moderate, spicy.

Petals:

*Texture.*—Thick, leathery.

*Shape.*—Orbicular.

*Surface.*—Smooth.

*Margin.*—Entire.

*Apex shape.*—Rounded.

*Base shape.*—Rounded.

*Form.*—Tips slightly recurved.

*Arrangement.*—Imbricated.

*Petaloids.*—Number: 0–2. Color: Same as petals.

*Persistence.*—Petals drop off cleanly before drying.

*Lastingness.*—On the plant: Fair (about 6–7 days). As a cut flower: Fair (about 7–8 days).

Reproductive parts:

*Stamens.*—Number: 91–100. Length: 8 mm. Anthers: Length: 2–3 mm. Color: Yellow-Orange Group 15C. Arrangement: Regular around styles. Filaments: Color: Red Group 45D. Length: 4–5 mm. Pollen: Color: Yellow-Orange Group 20C.

*Pisitls.*—Number: 40–45. Length: 5 mm. Styles: Color: Red-Purple Group 185A. Length: 4 mm. Stigmas: Color: Yellow-White Group 158C. Length: 1 mm. Hips: None observed.

PLANT

*Form.*—Climber.

*Growth.*—Vigorous, upright, branching.

*Age of maturity.*—3 years.

*Mature plant.*—Height: 3–4 meters, if trained vertically. Width: 2–3 meters, if trained vertically.

*Rootstock.*—Own roots.

Foliage: Number of leaflets on normal mid-stem leaves: 5 or 7.

*Size.*—Medium. About 130–140 mm long×110–120 mm wide.

*Quantity.*—Normal.

*Color.*—New foliage: Upper side: Greyed-Purple Group 183B. Lower side: Greyed-Purple Group 183B. Old foliage: Upper side: Green Group 139A. Lower side: Green Group 139B.

Leaflets:

*Size.*—About 60 mm long×30 mm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Yellow-Green Group 146D.

*Petiole rachis.*—Color: Yellow-Green Group 146D. Underside: Smooth.

*Auricles.*—None.

*Stipules.*—Length: 15 mm.

*Disease resistance.*—Resistant to powdery mildew and rust and susceptible to blackspot under normal growing conditions.

*Pest resistance.*—Not observed.

*Vein color.*—Green Group 139B.

*Venation pattern.*—Reticulate.

Wood:

*New wood.*—Color: Greyed-Purple Group 183B. Bark: Smooth.

*Old wood.*—Color: Green Group 137C. Bark: Smooth.

Prickles:

*Quantity.*—On main canes from base: 10–12 prickles per 15 cm. stem. On laterals from main canes: 10–12 prickles per 15 cm. stem.

*Form.*—Hooked slightly downward.

*Length.*—6–8 mm.

*Color when young.*—Greyed-Red Group 181A.

*Color when mature.*—Greyed-Yellow Group 161B.

Small prickles:

*Quantity.*—On main stalks: None. On laterals: None.

Winter hardiness: Hardy to Zone 5.

I claim:

1. A new and distinct variety of rose plant of the climber class, substantially as herein shown and described, characterized particularly by its large, yellow flowers produced on long climbing canes; moderate spicy scent; recurrent bloom; and resistance to rust and powdery mildew.

* * * * *

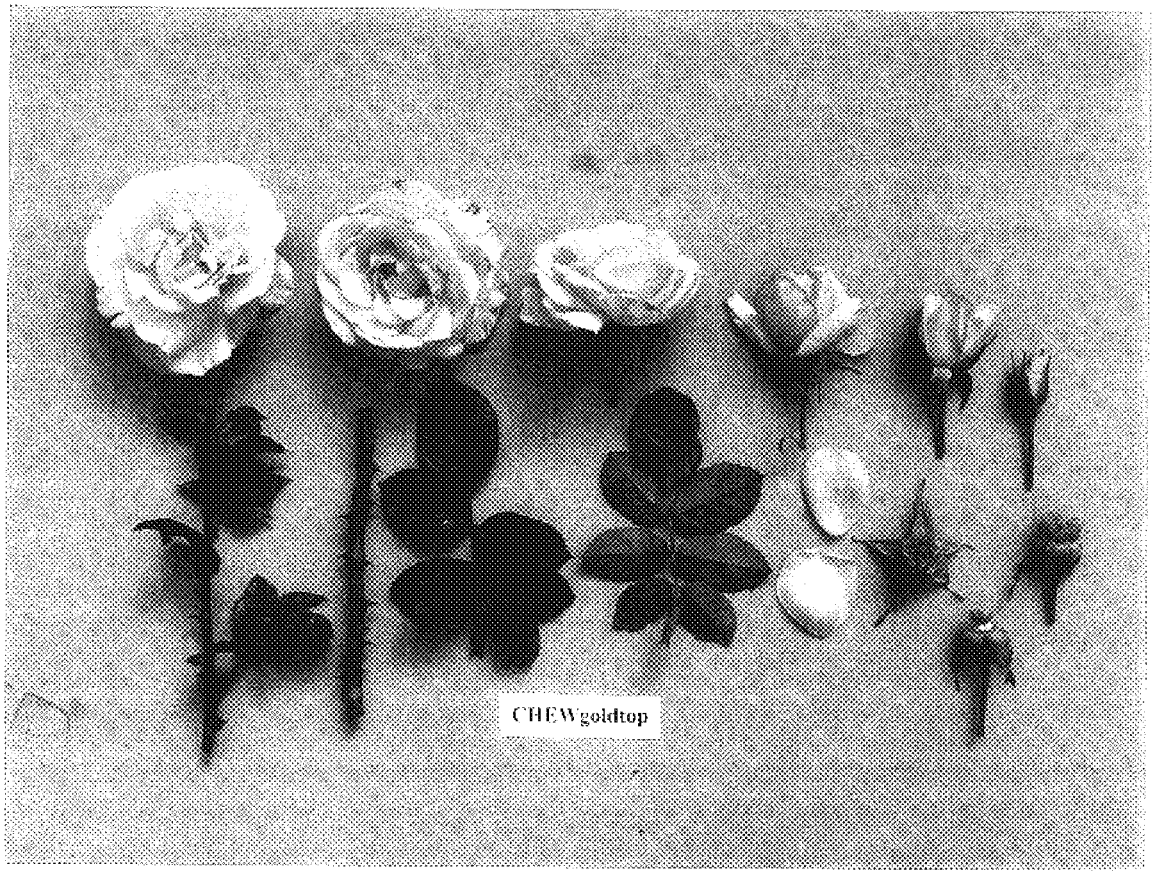
CHEWgoldtop